(12) United States Patent
Fernandez

(10) Patent No.: US 7,833,227 B2
(45) Date of Patent: Nov. 16, 2010

(54) CABLE AND CRIMP FOR BONE SURGERY

(75) Inventor: Alberto Fernandez, Montevideo (UY)

(73) Assignee: Synthes USA, LLC, West Chester, PA (US)

( * ) Notice: Subject to any disclaimer, the term of this patent is extended or adjusted under 35 U.S.C. 154(b) by 1158 days.

(21) Appl. No.: 11/248,418

(22) Filed: Oct. 13, 2005

(65) Prior Publication Data

US 2007/0100345 A1    May 3, 2007

(51) Int. Cl.
*A61B 17/82* (2006.01)
*F16G 11/00* (2006.01)
(52) U.S. Cl. .................. 606/74; 24/115 R; 24/129 R; 24/129 A; 24/129 B; 24/130
(58) Field of Classification Search ............... 606/74; 24/129 R, 130, 129 B, 129 A
See application file for complete search history.

(56) References Cited

U.S. PATENT DOCUMENTS

| | | | | |
|---|---|---|---|---|
| 131,593 | A | * | 9/1872 | Bowers ................. 24/129 R |
| 1,753,901 | A | * | 4/1930 | Neuberger ............. 24/129 R |
| 2,503,151 | A | * | 4/1950 | Ehmann ................ 24/115 R |
| 2,518,276 | A | * | 8/1950 | Brawand .............. 24/129 R |
| 3,239,900 | A | * | 3/1966 | Bottoms ............... 24/115 R |
| 3,654,668 | A | * | 4/1972 | Appleton ............... 24/16 R |
| 4,540,209 | A | * | 9/1985 | Cody ..................... 294/74 |
| 4,850,084 | A | * | 7/1989 | Iwasaki ................. 24/115 R |
| 4,930,193 | A | * | 6/1990 | Baker ................... 24/129 R |
| 5,339,498 | A | * | 8/1994 | Parsons ................. 24/129 R |
| 5,415,658 | A | | 5/1995 | Kilpela et al. |
| 5,423,820 | A | | 6/1995 | Miller et al. |
| 5,649,927 | A | | 7/1997 | Kilpela et al. |
| 5,653,711 | A | | 8/1997 | Hayano et al. |
| 5,836,061 | A | * | 11/1998 | Castillo et al. ............. 24/702 |
| 6,017,347 | A | | 1/2000 | Huebner et al. |
| 6,077,268 | A | | 6/2000 | Farris et al. |
| 6,387,099 | B1 | | 5/2002 | Lange et al. |
| 2006/0106391 | A1 | * | 5/2006 | Huebner .................. 606/74 |

OTHER PUBLICATIONS

International Search Report for PCT/US2006/040147 (PCT claiming priority to the present U.S. application), Mar. 15, 2007.

* cited by examiner

*Primary Examiner*—Thomas C Barrett
*Assistant Examiner*—Sameh Boles
(74) *Attorney, Agent, or Firm*—Fay Kaplun & Marcin, LLP

(57) ABSTRACT

A surgical cable and crimp device is provided. The cable has an enlargement (bead) affixed to one of its ends. The crimp member includes two holes. One of the holes includes a slot and a cavity. The cavity is sized to accept the bead of the cable, and the slot is sized to receive the flexible cable but not allow the bead to pass through. The other hole is a simple through hole. The cable can be inserted to loop the bone isolated from the crimp member. After the beaded end of the surgical cable is fastened to the crimp, the cable is passed through the simple through hole. The cable is then tensioned by the application thereto of a tensioning tool with the tool applied to the cable and to an abutment face of the crimp member.

9 Claims, 14 Drawing Sheets

CABLE AND CRIMP FOR BONE SURGERY

FIELD OF THE INVENTION

The present invention relates to orthopedics, and, more particularly, to a method and apparatus for securing surgical cable around bone.

BACKGROUND OF THE INVENTION

The use of surgical cable and crimp assemblies to fix bone parts and to join them together until the bone heals is a well-known technique. Surgical procedures on and in the vicinity of a bone with closely neighboring nerves, arteries, muscle, ligaments, complicated anatomical structures, and delicate areas represent a difficult and time consuming task for the surgeon. Thus it is important for the cable and crimp device to be assembled accurately, minimizing stress, trauma, risk, and injury to a patient, and with little difficulty for a surgeon performing such procedures, in as rapid a timeframe as possible.

Furthermore it is desirable to maintain the bulk of the cable, as well as the joint where the cable is affixed to itself, as compact as possible to minimize discomfort to the patient and damage to the surrounding tissue.

The orthopedic procedure is as follows: the cable, isolated from the crimp member, is inserted to loop around the bone in a minimally invasive way. After the cable is looped around the bone, its beaded first end is inserted into the cavity of the first hole of the crimp member. The slot at the first hole of the crimp member allows the first end of the cable to slide in place until the bead locks in its final position. The second end of the cable is then inserted through the second hole of the crimp member. Then the cable is tensioned by application of a tensioning tool either directly to the cable or through a provisional crimp, to an abutment face of the crimp close to the second hole of the crimp member. Once the desired final tension is established, the crimp member is crimped into the cable, the tensioning tool is removed, and the free end of the cable at the abutment face of the crimp is cut off.

Different surgical tools have heretofore been known. However, none of the tools adequately satisfies these aforementioned needs. Most of the prior art surgical tools require pulling from both cable ends, after the cable is looped around the bone, as those disclosed in U.S. Pat. Nos. 5,649,927 and 6,017,347. These kinds of devices have the problem of requiring significant spreading of the incision and muscle trauma. As a result, they are not a good solution for work in restricted areas.

Other devices permit tensioning of the cable by application of a tensioning tool to one of the cable ends and to an abutment face of the crimp by using a surgical cable which is factory crimped to one of the holes of the crimp, as those disclosed in U.S. Pat. Nos. 5,423,820, 6,077,268 and 6,387,099. The same effect is achieved by instruments that use a wire with a beaded end, as that disclosed in one embodiment of U.S. Pat. No. 6,017,347. The bead locks into the end of the crimp preventing the wire from sliding out of the crimp.

The option of pulling the cable by application of a tensioning tool to only one of the cable ends and to an abutment face of the crimp provides marked improvement over pulling from both cable ends when working in a restricted area.

The effectiveness of the surgical cable and crimp assemblies has proven itself, but an improved surgical crimp is needed. The prior art instruments fail to provide an adequate technique and lengthen the overall procedure significantly. Thus there exists the need for an improved surgical crimp: compact, strong and easy to assemble in a confined area that allows the insertion of the surgical cable to loop the bone isolated from the crimp member, and to connect one of the cable ends to the crimp after the cable is looped around the bone.

For the foregoing deficiencies in the prior art, a new cable and crimp assembly is needed which permits insertion of a surgical cable and looping of the cable around a bone while the cable is isolated from the crimp member, and, only after the cable is looped around the bone, permits the connection of one of the cable ends to the crimp member.

SUMMARY OF THE INVENTION

Accordingly, it is an object of the present invention to provide a simple and effective tool and method for securing surgical cable around bone without requiring a large incision for the tool to be assembled.

Another object of the invention herein is to provide an instrument and method wherein the exposure or stripping of the musculature away from the bone is minimized.

It is also an object of the present invention to provide a cable and crimp assembly which is compact, which is easy to assemble, which securely fastens the cable around the bone while maintaining the desired level of tension in the cable, and which has the highest possible resistance to tensile forces.

Furthermore, it is an object of the present invention to provide a cable and crimp assembly that enables the cable to be inserted isolated from the crimp member, and the crimp member to be attached to the surgical cable only after the cable is looped around the bone.

A preferred embodiment of the present invention comprises two members: a flexible cable and a crimp member. The surgical cable has an enlargement (a bead) affixed to its first end. The crimp member has a first hole and a second hole. The first hole is slotted and has a proximal and a distal part. The proximal part of the first hole has a cavity sized to accept the beaded end of cable. The distal part of the first hole is sized to allow the flexible cable to pass through, while the larger beaded first end of the cable is stopped. The second hole is non-slotted and sized to accommodate the cable. There is an abutment face on the crimp member located near the second hole.

The present invention creates an easy and straightforward procedure for the surgeon. This makes the crimp and cable technique simple and fast, overcoming one of the most important obstacles of actual surgery, time shortening.

By fulfilling the recently mentioned objects, the present invention is extremely helpful to the medical care area.

Other objects, advantages and novel features of the present invention will become apparent from the following detailed description of the invention when considered in conjunction with the accompanying drawings.

BRIEF DESCRIPTION OF THE DRAWINGS

Preferred embodiments of the present invention are disclosed in the accompanying drawings, wherein similar reference characters denote similar elements throughout the several views, and wherein.

DETAILED DESCRIPTION OF THE PREFERRED EMBODIMENTS

Hereinafter, a method for securing surgical cable around a bone according to a preferred embodiment of the present invention will be explained with reference to FIGS. 1-6.

Figure 1:
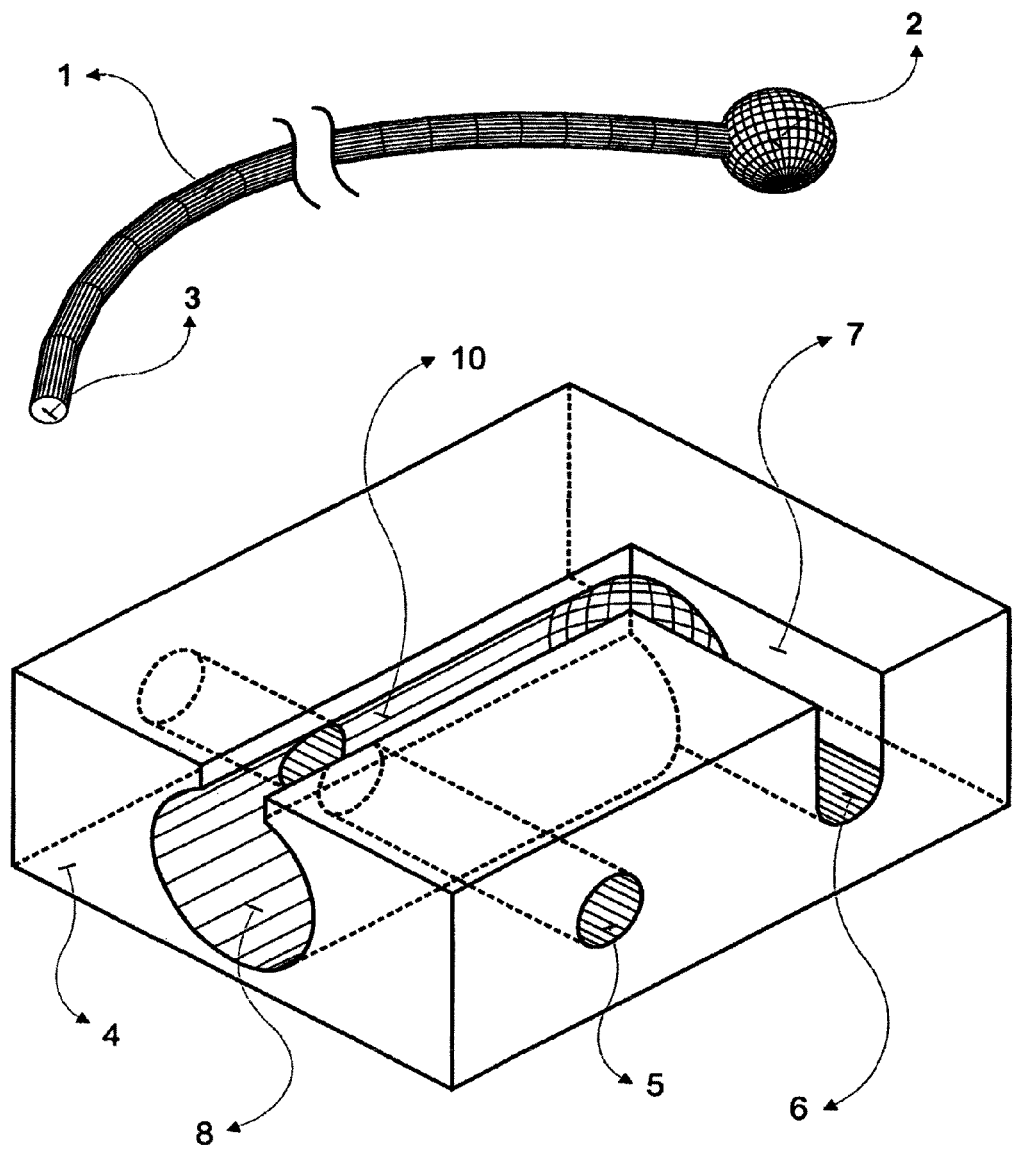
FIG. 1 is a perspective view of a surgical cable and crimp device according to a preferred embodiment of the present invention, wherein the flexible cable and the crimp member are shown.
Figure 2:
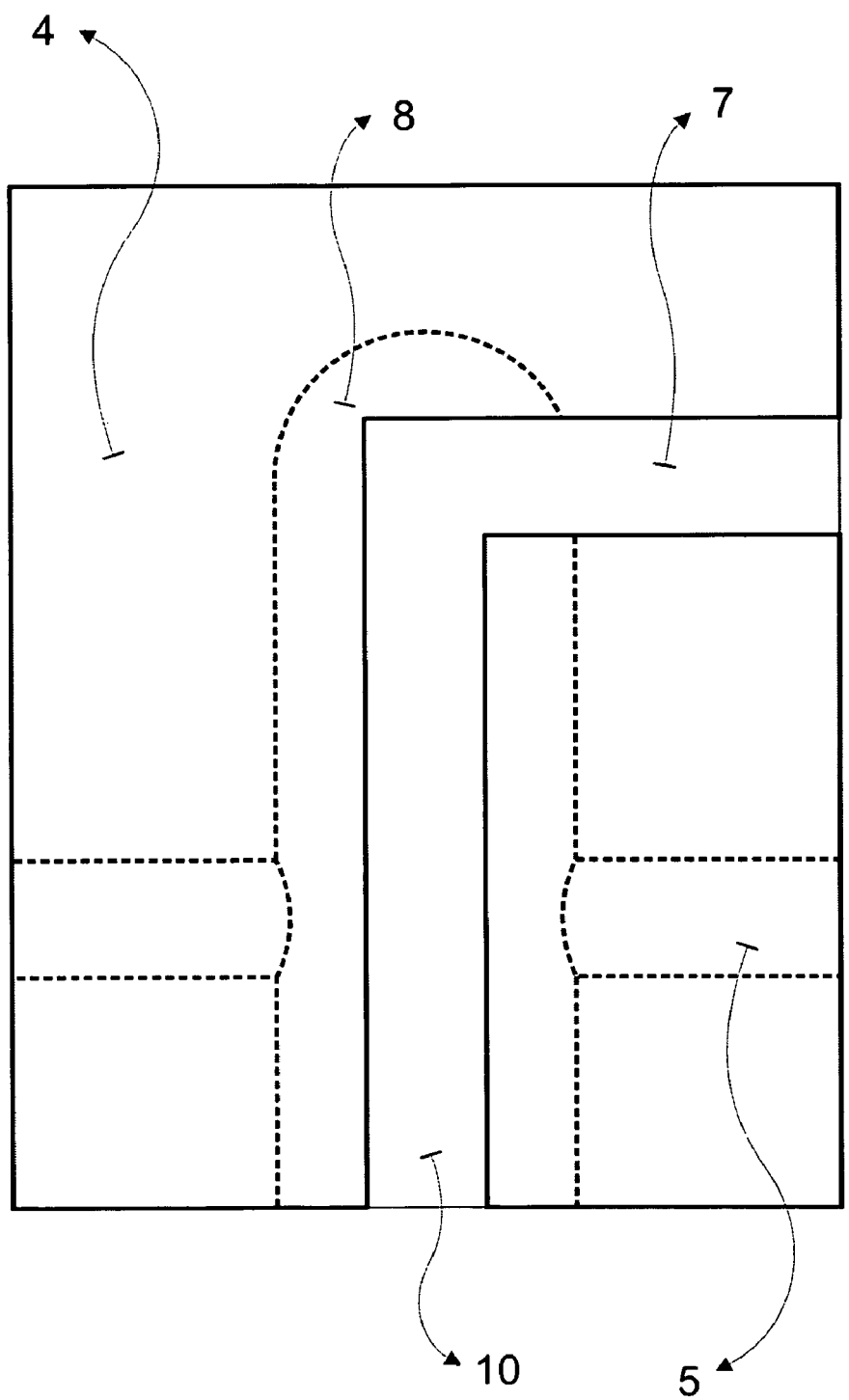
FIG. 2 is a top view of the crimp member shown in FIG. 1, prior to assembling with the flexible cable.

FIG. 1 shows a preferred embodiment of the cable and crimp assembly of the present invention, disassembled. The flexible cable 1 has two ends—a first beaded end 2, and a second end 3. The crimp member 4 has a first hole 6 and a second hole 5. The second hole 5 is a simple through hole sized to accept the flexible cable 1. The first hole 6 is a complex two arms slotted hole. In the distal part of the hole 6, the slot 7 is sized to accommodate the cable, but not allow the enlargement (bead) 2 existing at the first end of the flexible cable 1 to pass through. The cavity 8 is located at the proximal arm of the hole, and is sized to accept the beaded first end of the cable 2.

Figure 3:
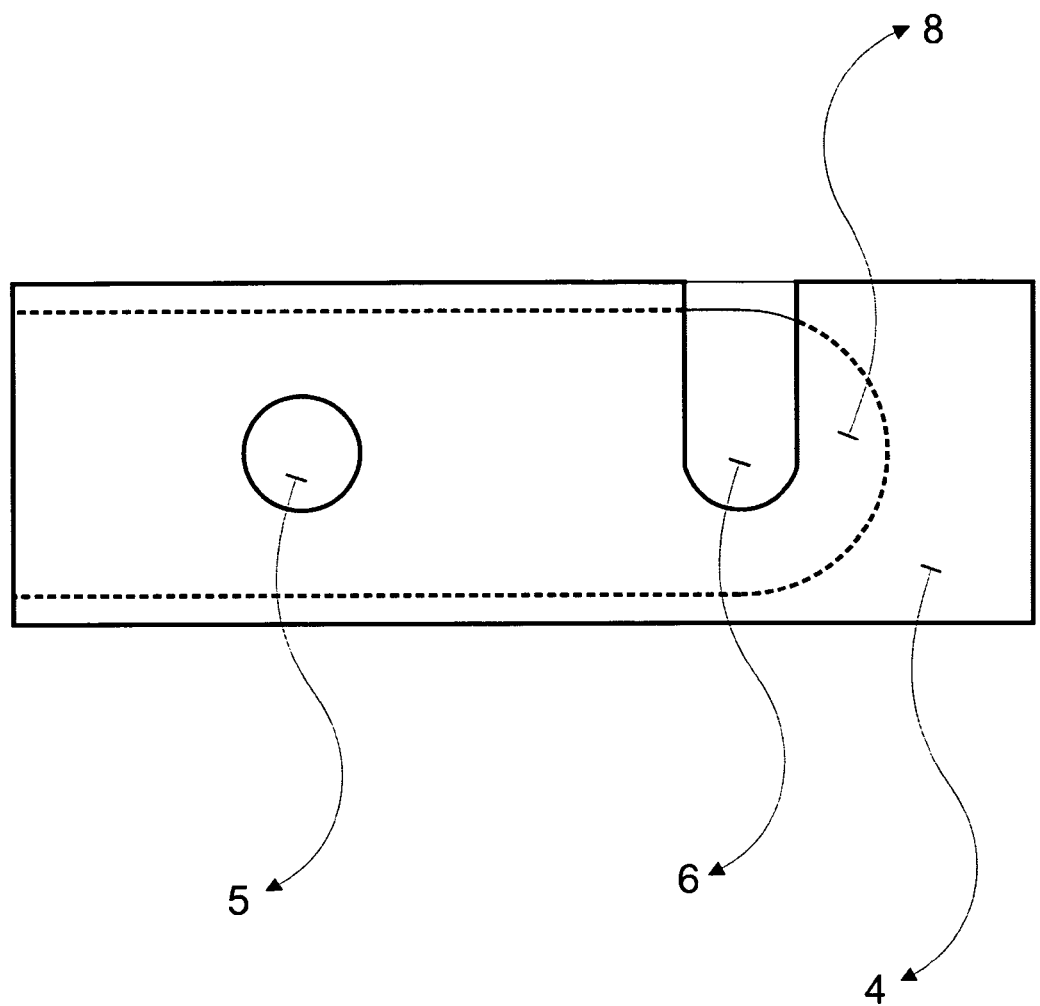
FIG. 3 is a side view of the crimp member shown in FIG. 1.

The different sizes of the two arms of the slotted hole 6 are clearly seen in FIG. 3.

Figure 4:
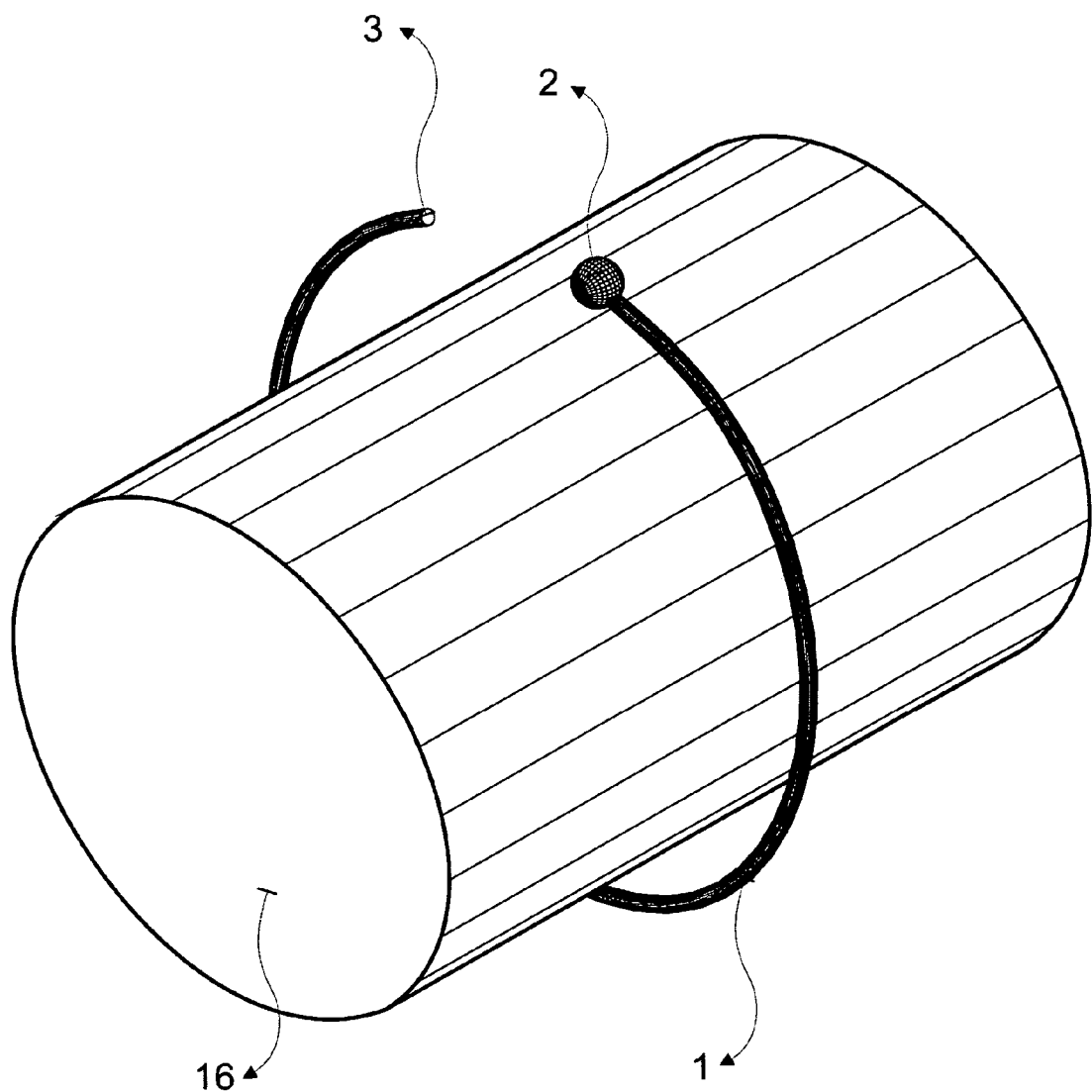
FIG. 4 is a perspective view of a preferred embodiment of the flexible cable of the present invention, isolated from the crimp, looped around the bone.
Figure 5:
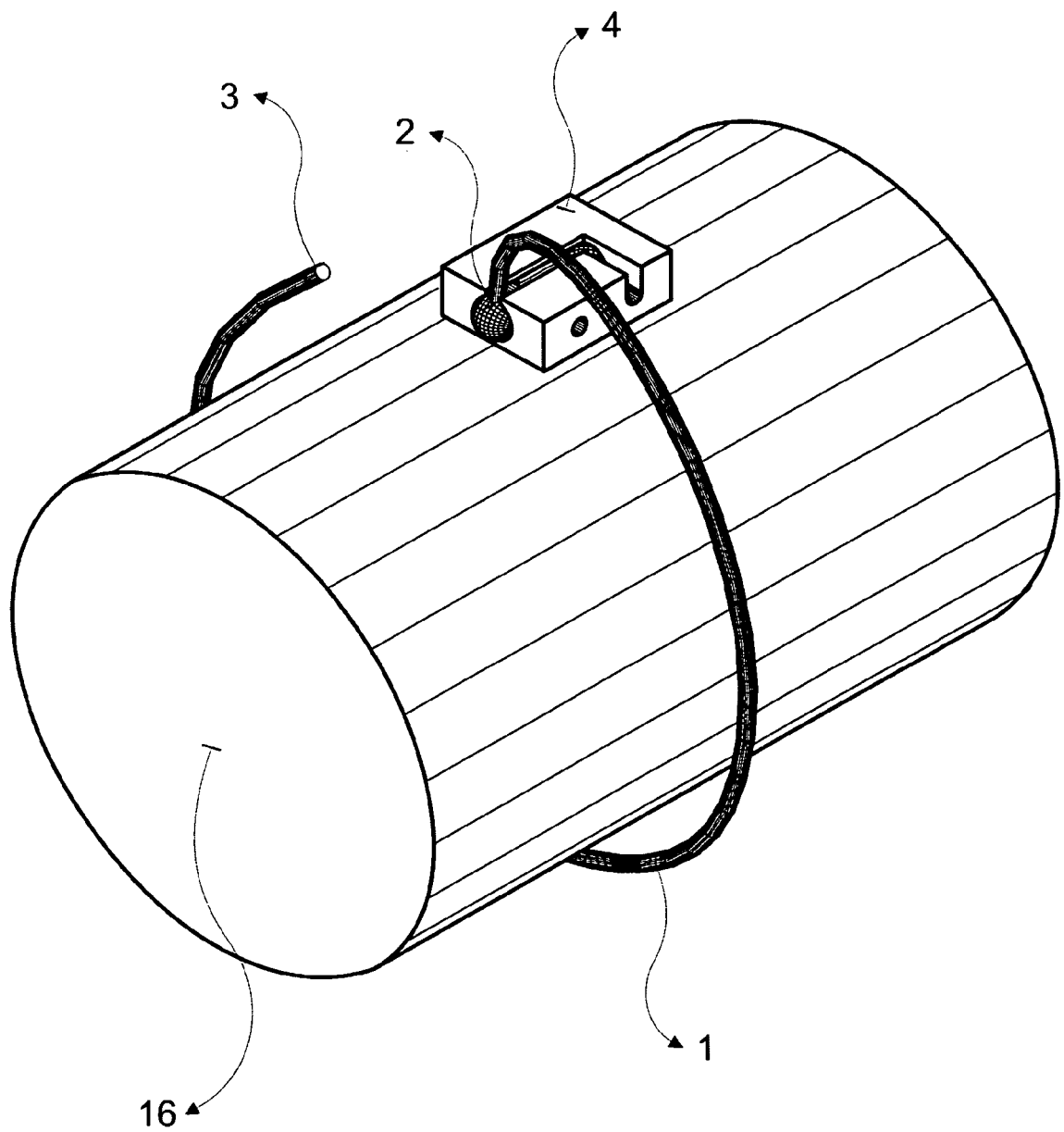
FIG. 5 is a perspective view of the crimp member shown in FIG. 1, wherein the first beaded end of the cable is partially inserted into the crimp member.
Figure 6:
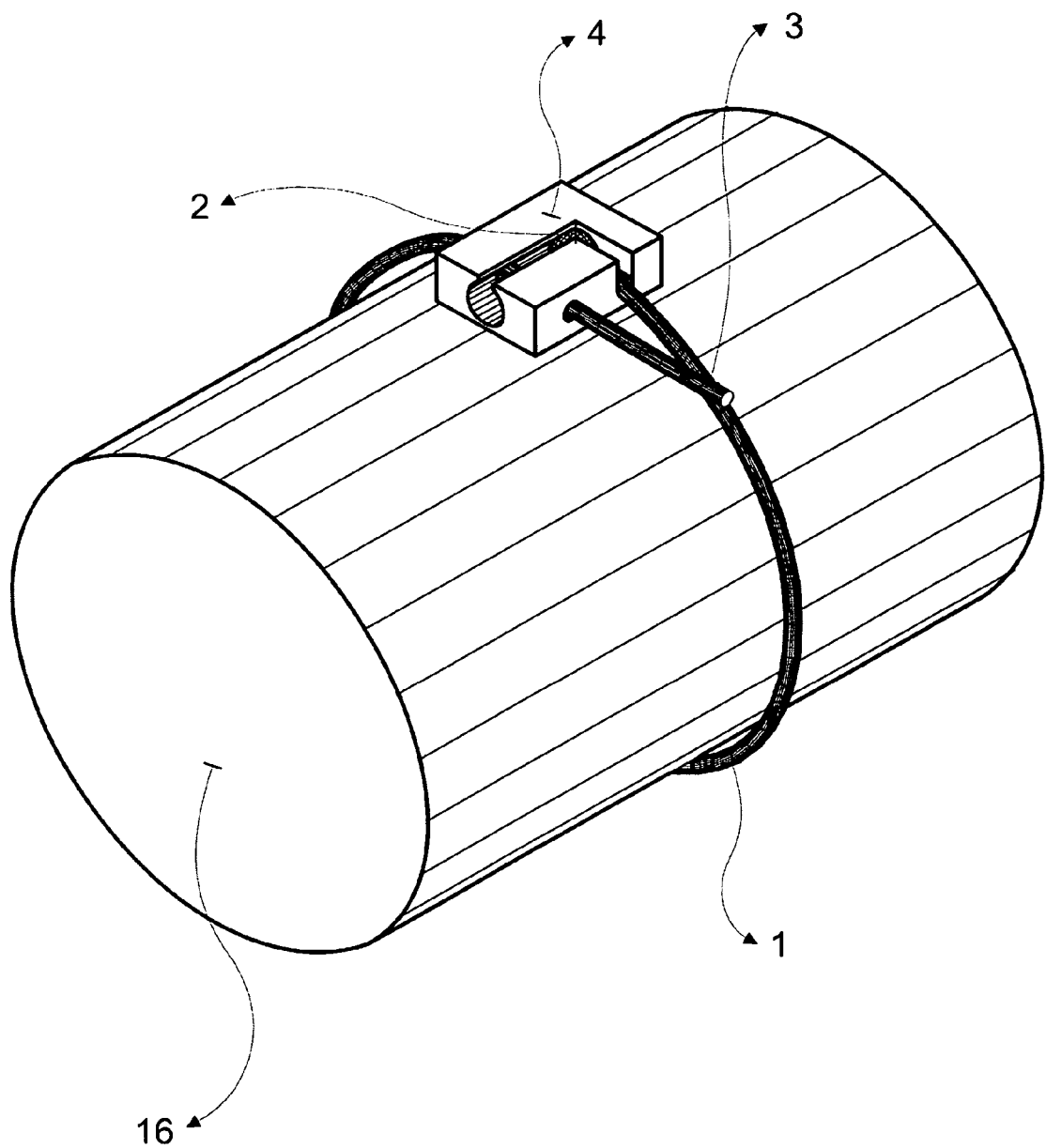
FIG. 6 is a perspective view of a cable and crimp device according to the preferred embodiment shown in FIG. 1, wherein the flexible cable is already inserted into the crimp member and is ready to be tensed.
Figure 7:
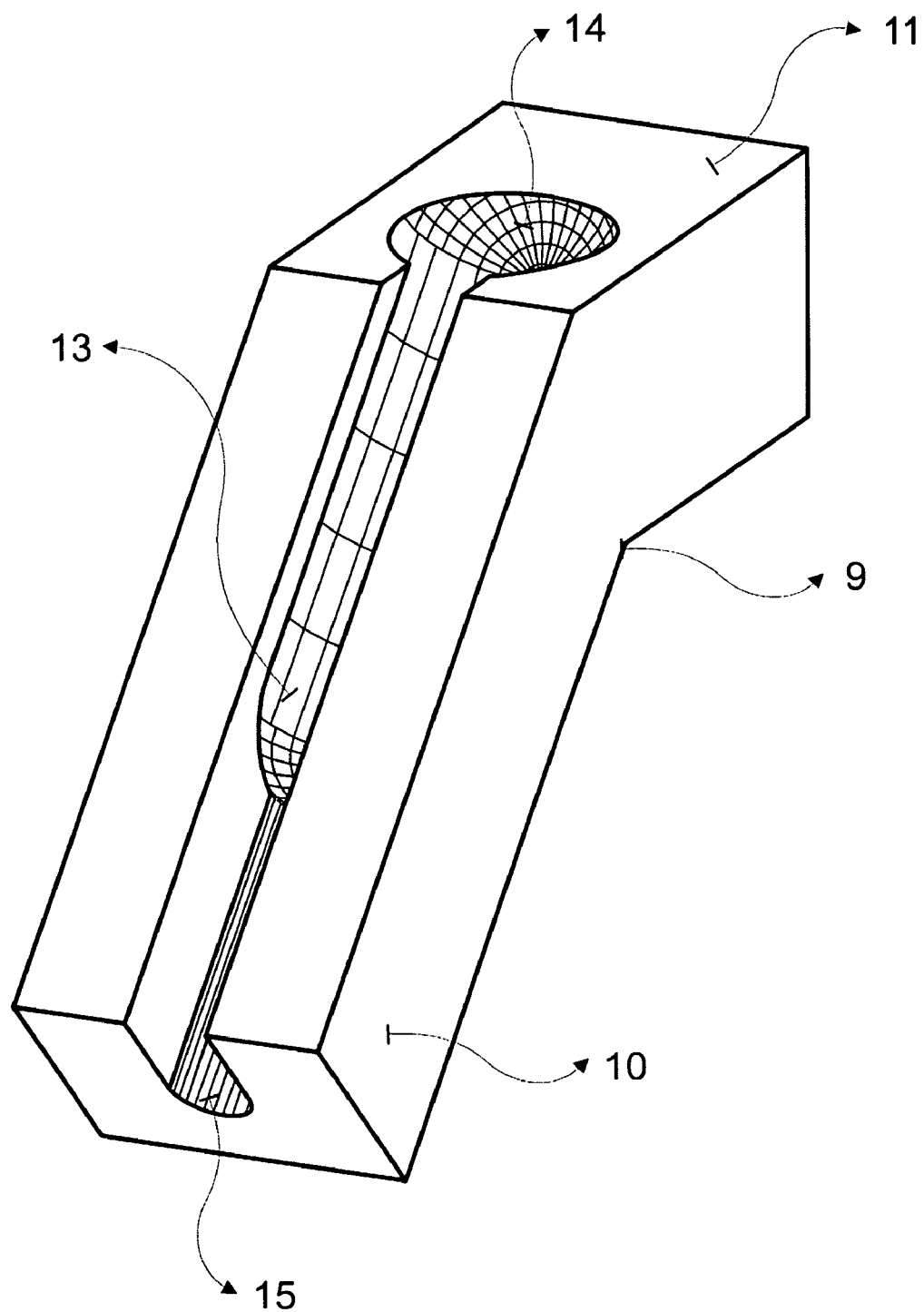
FIG. 7 is a perspective view of another preferred embodiment of the crimp member of the present invention.
Figure 8:
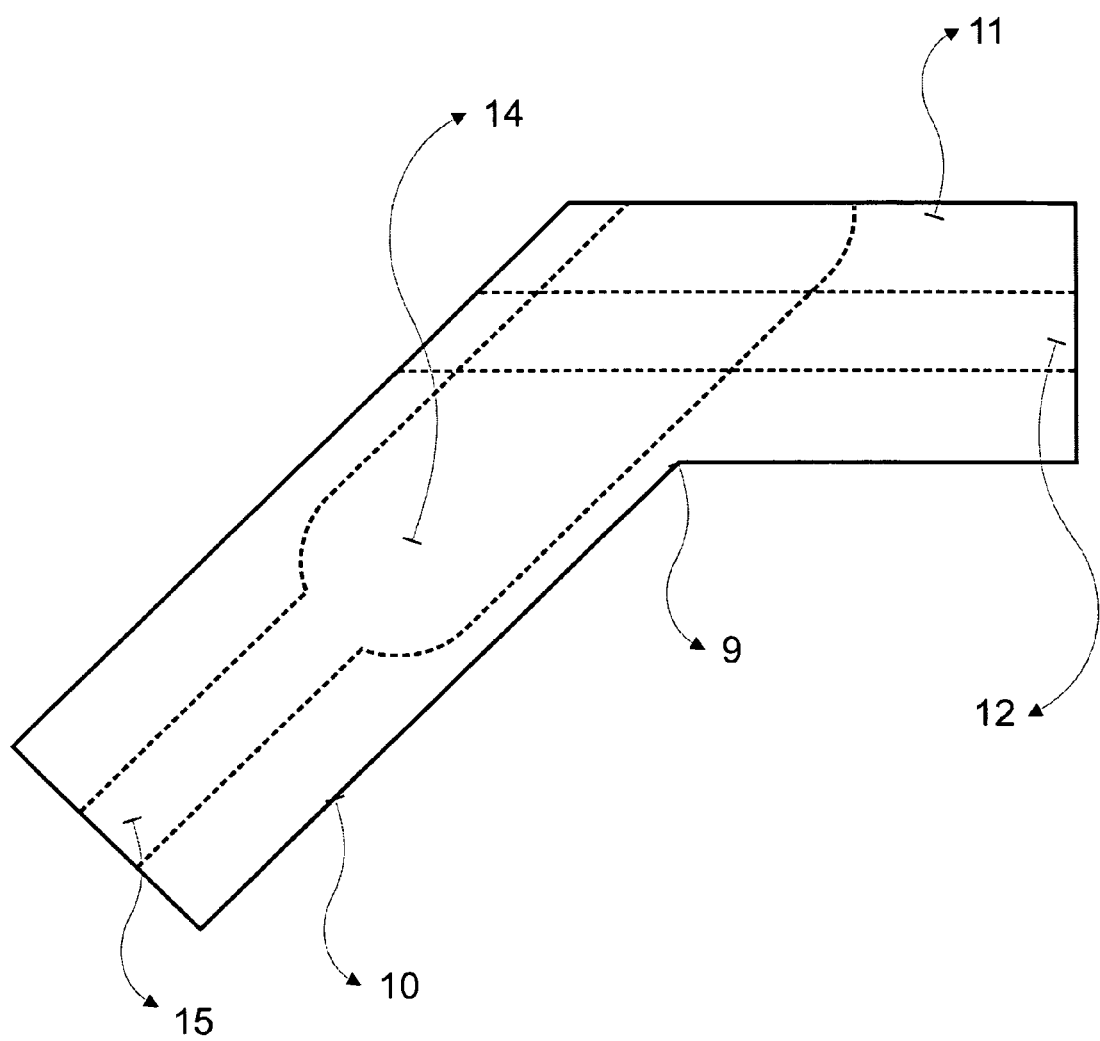
FIG. 8 is a side view of the crimp member shown in FIG. 7.
Figure 9:
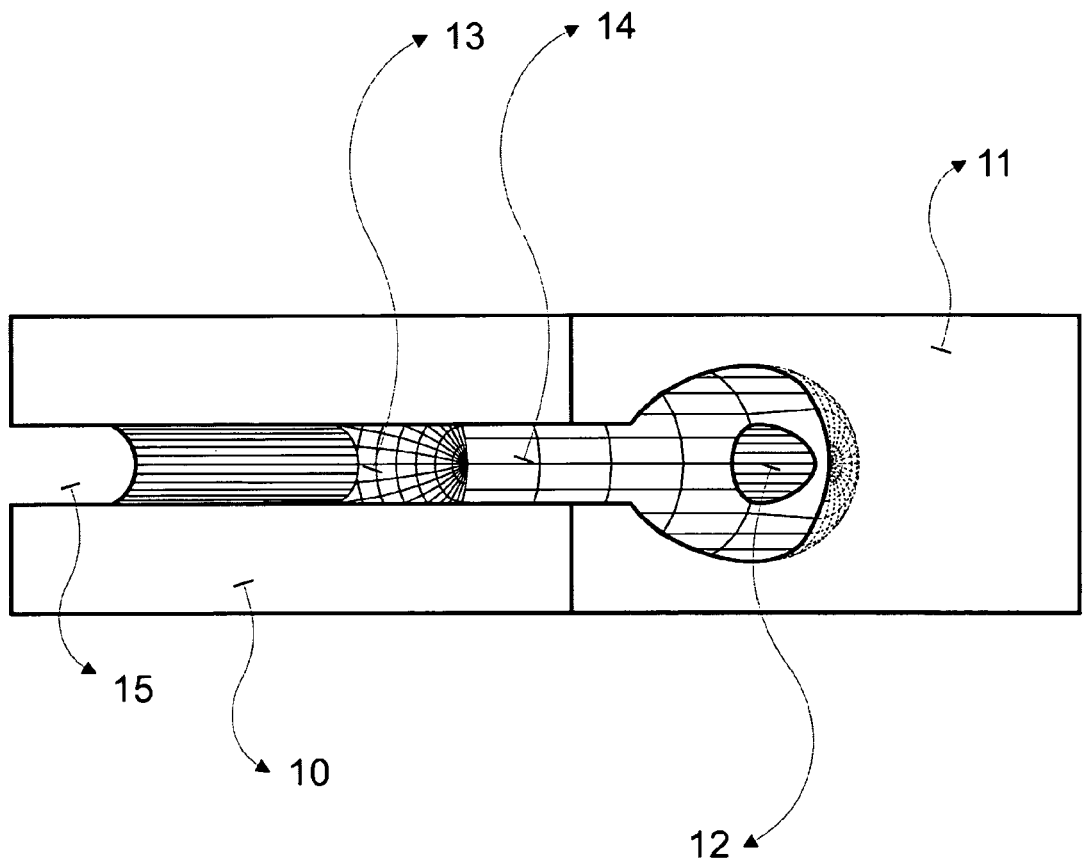
FIG. 9 is a top view of the crimp member shown in FIG. 7.
Figure 10:
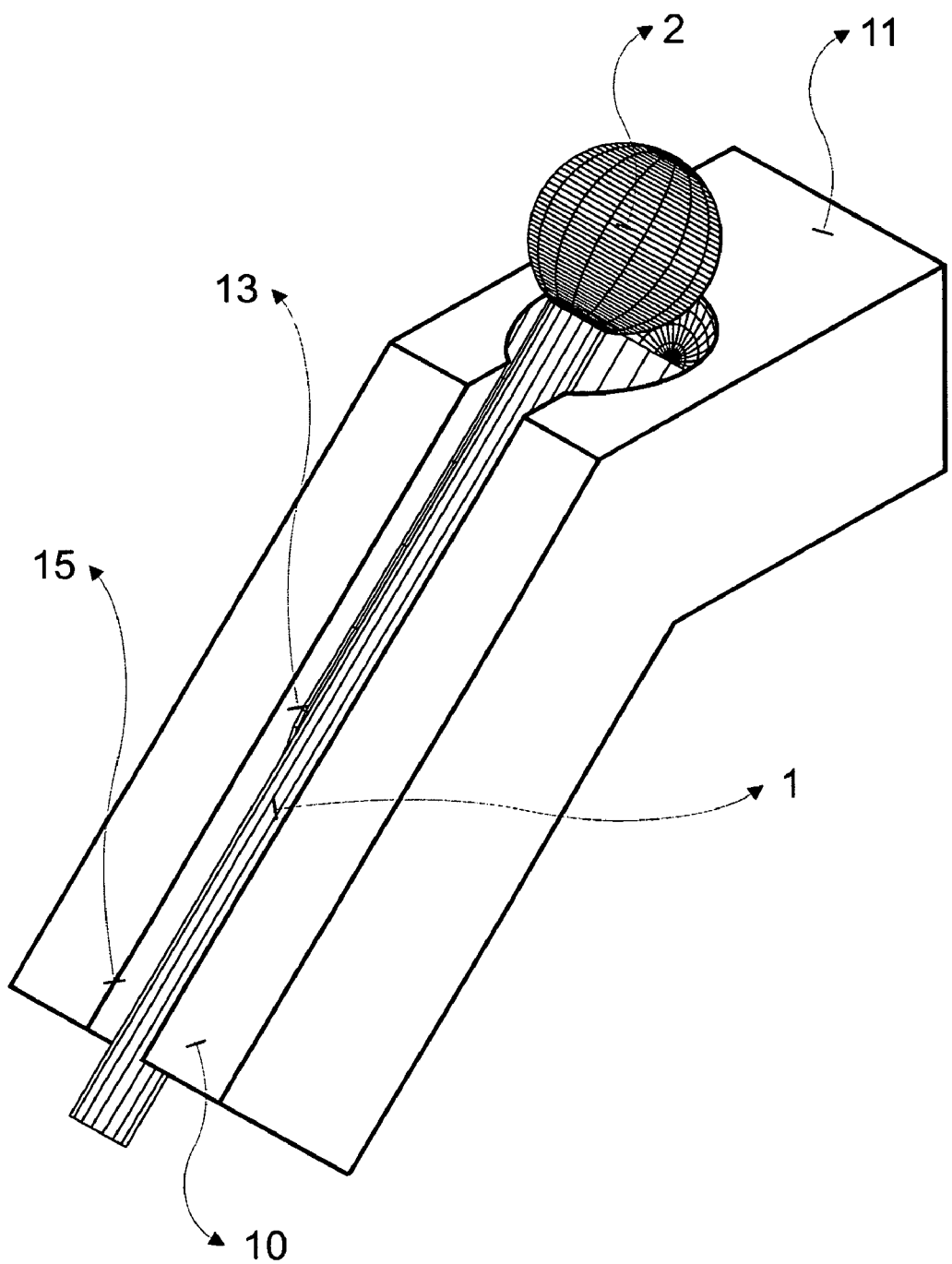
FIG. 10 is a perspective view of the crimp member shown in FIG. 7, wherein the flexible cable is partially inserted into the crimp member.
Figure 11:
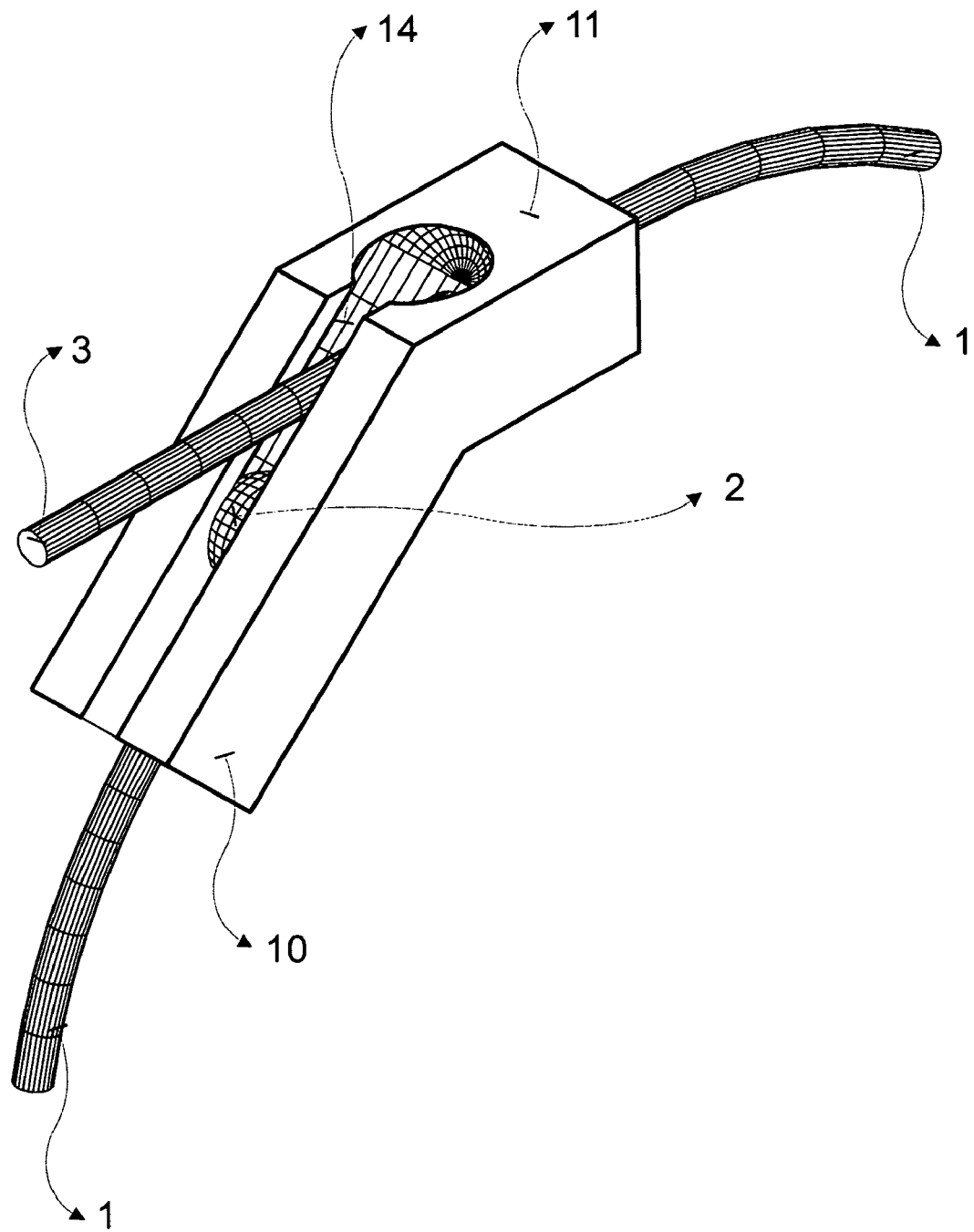
FIG. 11 is a perspective view of the crimp member of FIG. 7, wherein the flexible cable is completely inserted into the crimp and is ready to be tensed.

A preferred surgical procedure is described herein with reference to FIGS. 4-6.

The preferred surgical technique starts with the insertion of the flexible cable 1, isolated from the crimp member 4, around the bone to be cerclaged 16, as shown in FIG. 4

After the flexible cable 1 is looped around the bone to be cerclaged 16, the first beaded end 2 of the flexible cable 1, is inserted into the cavity 8 of the crimp member 4 as shown in FIG. 5. The flexible cable 1 is then pulled in position emerging from the crimp 4 at the distal part of the first hole 6 of the crimp 4. Then the second end 3 of the flexible cable 1 is passed through the second hole 5, as shown in FIG. 6. The cable and crimp device are then ready to be tensed.

Another preferred embodiment of the present invention is shown with reference to FIGS. 7-14.

The crimp member 9, shown in FIGS. 7-10, has a first arm 10 and a second arm 11. The first arm 10 has a slotted hole with a larger part 14 sized to accept the enlargement (bead) 2 existing at the first end of the flexible cable 1, and a smaller sized slotted hole 15 sized to accept the flexible cable 1. This hole has a slot as indicated at 13. The second aim 11 of the crimp member 9 has a simple through hole 12 sized to accept the flexible cable 1.

A preferred surgical procedure employing the embodiment shown in FIGS. 7-10 is described hereinto with reference to FIGS. 11-14.

Figure 12:
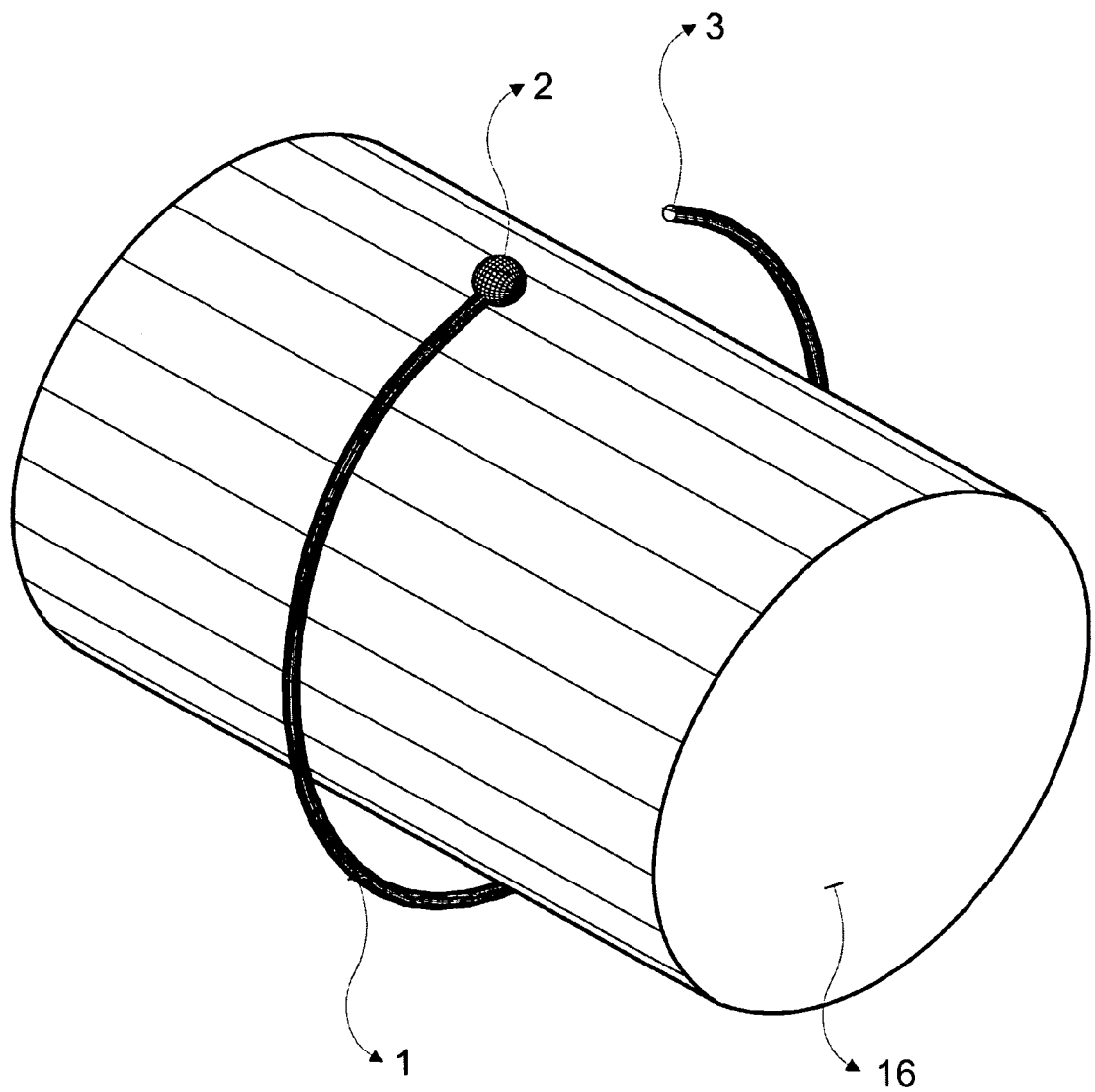
FIG. 12 is a perspective view of a preferred embodiment of the flexible cable of the present invention, isolated from the crimp member, looped around the bone.

The preferred surgical technique starts with the insertion of the flexible cable 1 isolated from the crimp member 9 around the bone to be cerclaged 16, as shown in FIG. 12

Figure 13:
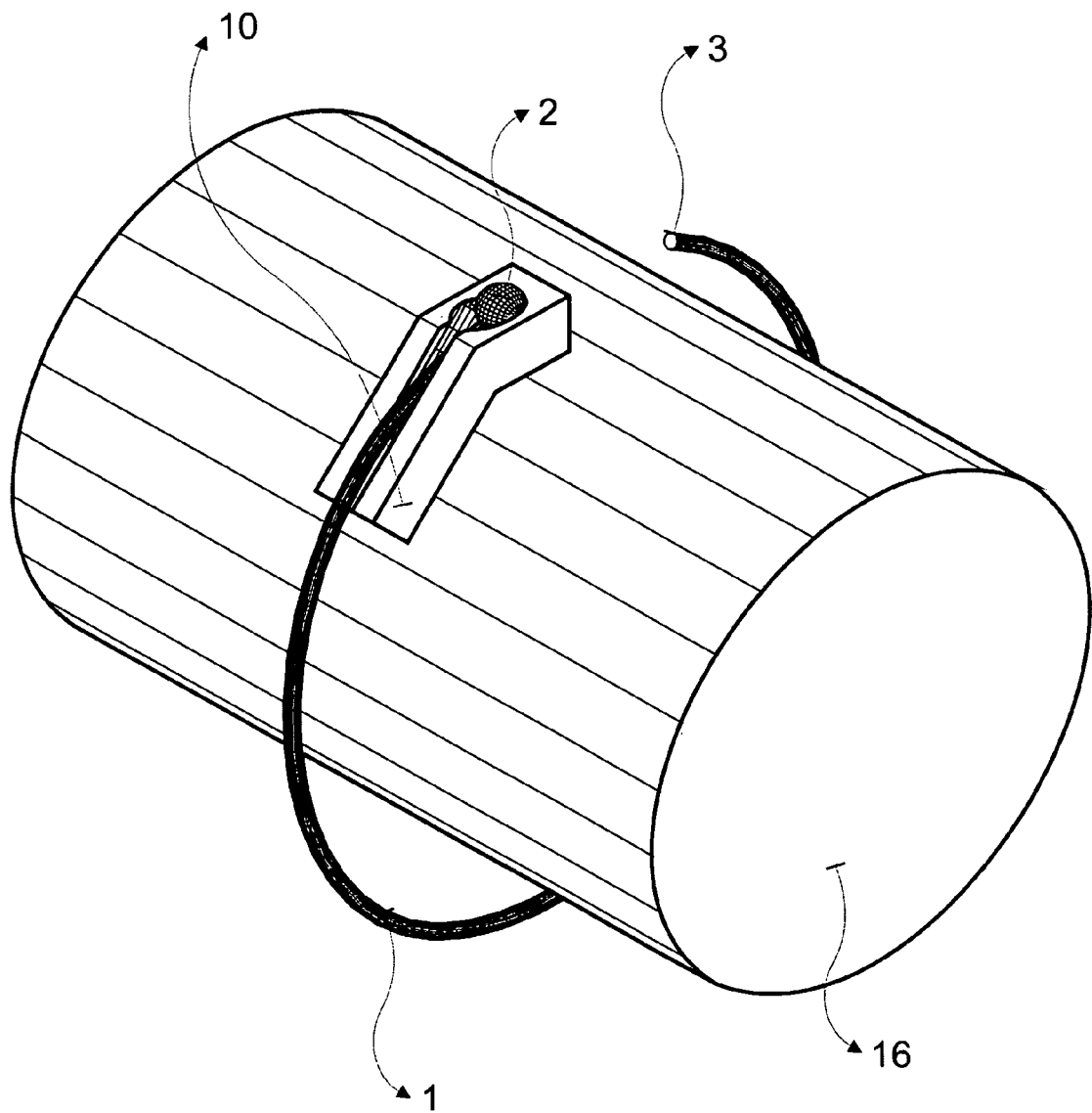
FIG. 13 is a perspective view of the cable and crimp device according to the preferred embodiment of the present invention shown in FIGS. 7 and 12, wherein the flexible cable is already looped around the bone and partially inserted into the crimp member.
Figure 14:
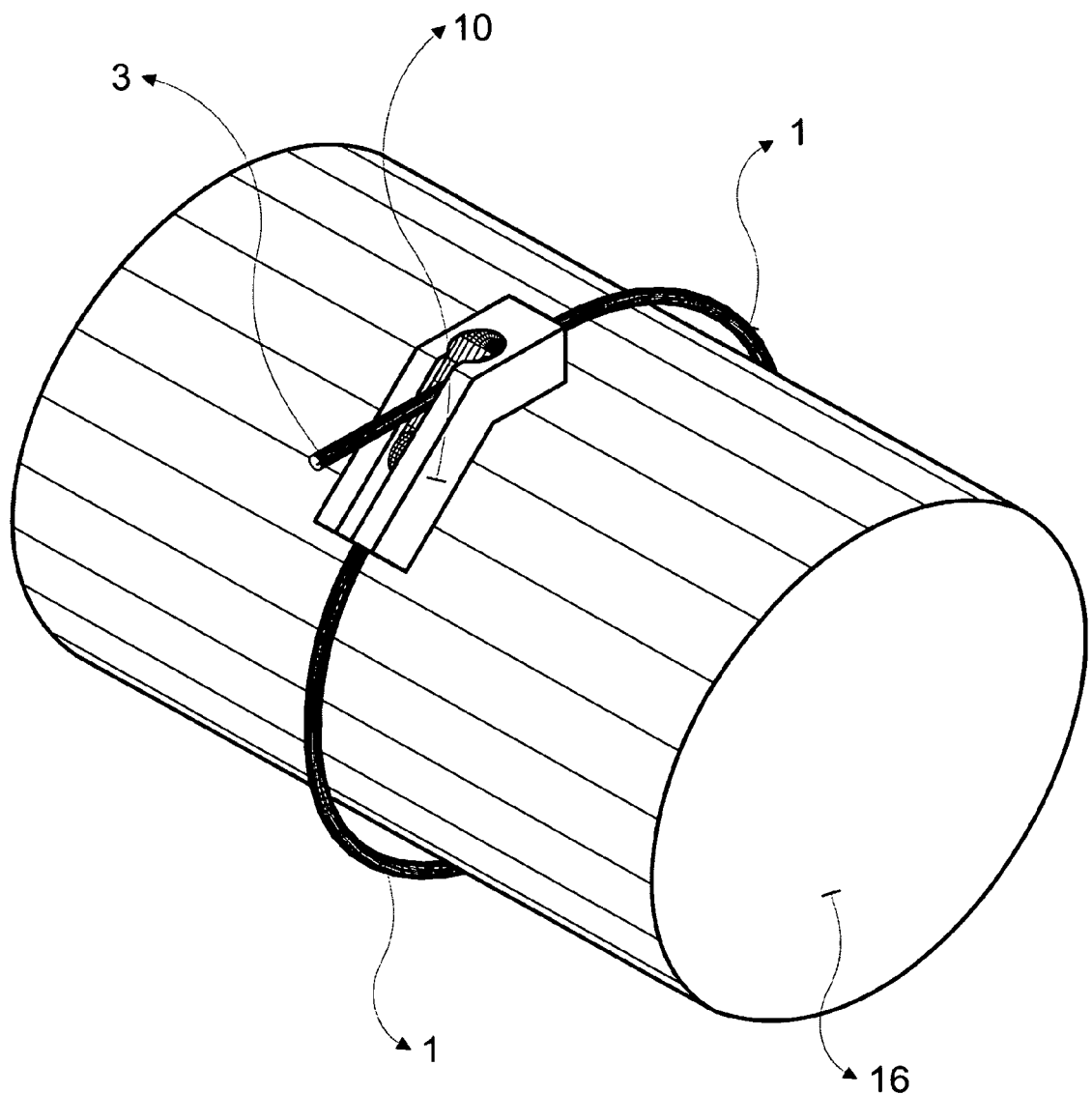
FIG. 14 is a perspective view of the cable and crimp device according to the preferred embodiment of the present invention shown in FIGS. 7 and 12, wherein the flexible cable is already inserted into the crimp and is ready to be tensed.

After the flexible cable 1 is looped around the bone to be cerclaged 16, the first beaded end 2 of the flexible cable 1, is inserted into the cavity 14 of the crimp 9 as shown in FIG. 13. The flexible cable 1 is then pulled in position to the slot of the hole 13. Then, the second end 3 of the flexible cable 1 is passed through the second hole 12 of the crimp member 9, as shown in FIG. 14. The flexible cable 1 is then tensioned by the application thereto of a tensioning tool with the tool applied to the flexible cable 1 and to an abutment face of the crimp member 9.

While I have illustrated and described preferred embodiments of the invention, it will be understood that those skilled in the art will thereby be enabled to devise variations and modifications without departing from the spirit and scope of this invention, as defined in the appended claims.

What I claim as my invention is:

1. A fastening apparatus for fixing bone elements comprising:
   a. a flexible cable having a first end, a second end, and a width, the first end including an enlargement greater than the width of the cable;
   b. a crimp member including
      i. a first hole having a length, a slot, a proximal opening formed on a first planar face of the crimp member and opening into a proximal portion of the slot, a distal opening formed on a second planar face of the crimp member and opening into a distal portion of the slot, and a planar opening formed on a third planar face of the crimp member and opening into the proximal and distal portions, wherein the third planar face is perpendicular to the first and second planar faces, the proximal opening being configured and dimensioned to accept the enlargement at the first end of the cable, the proximal portion of the slot being configured and dimensioned to permit the enlargement of the cable to pass therethrough, the planar opening being configured and dimensioned to permit the width of the cable to pass therethrough and prevent the enlargement from passing therethrough, and the distal portion of the slot configured and dimensioned to permit the width of the cable to pass therethrough and prevent the enlargement from passing therethrough, and
      ii. a second hole having a length, the second hole configured and dimensioned to permit insertion of the second end of the cable through the second hole.

2. The apparatus of claim 1, wherein the crimp member is configured for attachment to the flexible cable after the cable has been looped around a bone.

3. The apparatus of claim 2, wherein the crimp member is attached to the cable by insertion of the first end of the cable into the first hole of the crimp member and insertion of the second end of the cable through the second hole of the crimp member to form a loop of adjustable diameter.

4. The apparatus of claim 1, wherein the first and second holes of the crimp member are parallel straight holes.

5. The apparatus of claim 1, wherein the first and second holes of the crimp member are coplanar.

6. The apparatus of claim 1, wherein the proximal portion of the first hole is coplanar with the second hole.

7. The apparatus of claim 1, wherein the distal portion of the first hole is substantially parallel to the second hole.

8. A fastening apparatus for fixing bone elements comprising:
- a. a flexible cable having a width, an enlarged first end, and a second end; and
- b. a crimp member including
  - i. a first hole having a length, a proximal opening formed on a first planar face of the crimp member and opening into a proximal portion of the first hole, a distal opening formed on a second planar face of the crimp member and opening into a distal portion, and a planar opening formed on a third planar face of the crimp member and opening into the proximal and distal portions, wherein the third planar face is perpendicular to the first and second planar faces, the proximal portion of the first hole configured and dimensioned to accept the enlarged first end of the cable, the planar opening configured and dimensioned to permit the width of the cable to pass therethrough while preventing the enlarged first end to pass therethrough, and the distal portion of the first hole configured and dimensioned to prevent the enlarged first end from passing therethrough while permitting the width of the cable to pass therethrough, and
  - ii. a second hole having a length, the second hole configured and dimensioned to permit insertion of the second end of the cable through the second hole;

wherein the crimp member is configured for attachment to the flexible cable after the flexible cable has been wrapped around a bone.

9. The apparatus of claim 8, wherein the proximal portion of the first hole defines a first axis and the distal portion of the second hole defines a second axis, and the first and second axes are not collinear.

\* \* \* \* \*